United States Patent [19]

Blanchard et al.

[11] 4,054,582

[45] Oct. 18, 1977

[54] PROCESS FOR CONVERTING CIS-HEXAHYDRODIBENZO[B,D]PYRAN-9-ONES TO TRANS-HEXAHYDRODIBENZO[B,D]-PYRAN-9-ONES

[75] Inventors: William B. Blanchard; Charles W. Ryan, both of Indianapolis, Ind.

[73] Assignee: Eli Lilly and Company, Indianapolis, Ind.

[21] Appl. No.: 702,807

[22] Filed: July 6, 1976

[51] Int. Cl.$^2$ .......................................... C07D 311/78
[52] U.S. Cl. .................................................. 260/345.3
[58] Field of Search ...................................... 260/345.3

[56] References Cited

PUBLICATIONS

Razdan et al., Tetrahedron Letters, pp. 4947–4950, (1969).

*Primary Examiner*—James O. Thomas, Jr.
*Assistant Examiner*—Nicky Chan
*Attorney, Agent, or Firm*—CharlesW. Ashbrook; Everet F. Smith

[57] ABSTRACT

Reaction of cis-1-hydroxy-3-substituted-6,6-dimethyl-6,6a,7,8,10,10a-hexahydro-9H-dibenzo[b,d]pyran-9-ones with an aluminum halide in an unreactive organic solvent effects complete epimerization to provide the corresponding trans-1-hydroxy-3-substituted-6,6-dimethyl-6,6a,7,8,10,10a-hexahydro-9H-dibenzo[b,d]-pyran-9-one.

5 Claims, No Drawings

PROCESS FOR CONVERTING CIS-HEXAHYDRODIBENZO[B,D]PYRAN-9-ONES TO TRANS-HEXAHYDRODIBENZO[B,D]-PYRAN-9-ONES

BACKGROUND OF THE DISCLOSURE

The first interconversion of a cis-dibenzo[b,d]-pyran to the corresponding trans-isomer was accomplished by Razdan and Zitko when they converted cis-1-hydroxy-3-n-pentyl-6,6,9-trimethyl-6a, 7,8,10a-tetrahydro-6H-dibenzo-[b,d]pyran to the corresponding trans-6a, 7,10,10a-tetrahydro-dibenzo[b,d]pyran derivative. This interconversion was effected by treatment of the cis-isomer with boron tribormide in dichloromethane at $-20°$ C. for ninety minutes. The isomerization was accompanied by a double bond migration of the $\Delta^{9\,(10)}$ double bond to the $\Delta^{8\,(9)}$ position. The isomerization reaction of Razdan and Zitko is discussed more fully in Tetrahedron Letters, 4947–4950 (1960).

Treatment of a cis-1-hydroxy-3-substituted-6,6-dimethyl-6,6a,7,8,10,10a-hexahydro-9H-dibenzo[b,d]pyran-9-one, a compound differing from that of Razdan and Zitko by having a tetone group at the C-9 position instead of a methyl group, and a totally saturated C ring instead of having a double bond in the C ring, with boron tribromide under the reaction conditions taught by Razdon and Zitko fails to provide isolable quantities of the corresponding trans isomer. In fact, it recently has been discovered that reaction of a 5-substituted resorcinol with 1-methoxy-4-(1-hydroxy-1-methylethyl)-1,4,-cyclohexadiene in the presence of excess boron trifluoride provides almost exclusively a cis-1-hydroxy-3-substituted-6,6-dimethyl-6,6a,7,8,10,1-0a-hexahydro-9H-dibenzo[b,d]pyran-9-one, without any isomerization to the trans isomer taking place under the conditions of the reaction. Such condensation reaction is the subject of Day and Lavagnino's copending application filed this even date herewith.

Certain of the trans-1-hydroxy-3-substituted-6,6-dimethyl-6,6a,7,8,10,10a-hexahydro-9H-dibenzo [b,d]-pyran-9-ones have recently been found to be of particular importance is pharmacological agents, especially in the treatment of anxiety, depression, and for producing analgesia. The use of such trans-hexahydrodibenzopyranones is described in detail in U.S. Pat. Nos. 3,928,598, 3,944,673, and 3,953,603. While the corresponding cis-hexahydrodibenzopyranones possess useful pharmacological activity, such activity is suprisingly somewhat less than that of the corresponding trans-isomers. It is therefore an object of this invention to provide a convenient process for converting a cis-hexahydrodibenzopyranone to the pharmacologically more active trans isomer.

SUMMARY OF THE INVENTION

This invention provides a process for preparing a trans-hexahydrodibenzopyranone of the formula

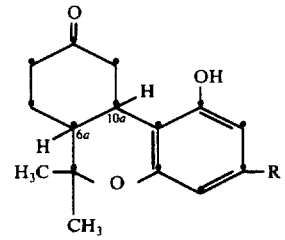

wherein R is $C_5$–$C_{10}$ alkyl, $C_5$–$C_{10}$ alkenyl, $C_5$–$C_8$ cycloalkyl, or $C_5$–$C_8$ cycloalkenyl, and wherein the hydrogen atoms attached at the 6a and 10a positions are oriented trans to one another; comprising reacting a 6a,10a-cis-hexahydrodibenzopyranone having the above formula, wherein the hydrogen atoms attached at the 6a and 10a positions are oriented cis to one another, with an aluminum halide selected from aluminum bromide and aluminum chloride in an unreactive organic solvent at a temperature within the range of from about $-80°$ C. to about 100° C., for a period of time ranging from about 10 minutes to about 6 hours, and recovering the thus formed 6a,10a-trans-1-hydroxy-3-substituted-6,6-dimethyl-6,6a,7,8,10,10a-hexahydro-9H-dibenzo[b,d]pyran-9-one therefrom.

DETAILED DESCRIPTION OF THE INVENTION

This invention provides a convenient process for preparing a 6a,10a-trans-hexahydro-dibenzo[b,d]pyran-9-one from the corresponding 6a, 10a-cis isomer. As used herein, the term "6a,10a-cis" and "6a,10a-trans" refers to the orientation relative to one another of the hydrogen atoms attached at the 6a and 10a position of a compound represented by the above formula. Accordingly, compounds which are designated as being "6a,1-0a-cis" are those compounds of the above formula wherein the hydrogen atoms attached at the 6a and the 10a positions are oriented on the same side of the plane of the molecule. It will be recognized that at least two isomers are included with the "6a,10a-cis" designation. In particular, both the 6a hydrogen atom and the 10a hydrogen atom can be oriented above the plane of the molecule, in which case their absolute configuration is designated as 6aβ and 10aβ. Alternatively, both the 6a hydrogen atom and the 10a hydrogen atom can be oriented below the place of the molecule, in which case they are designated as 6aα and 10aα. Similarly, the term "6a, 10a-trans" refers to those compound having the above formula in which the 6a and 10a hydrogen atoms are oriented trans to one another, that is to say they are oriented on opposite sides of the plane of the molecule. As in the case of the 6a,10a-cis designation, the 6a,10a-trans designation includes at least two isomers, namely that isomer in which the 6a-hydrogen is above the plane of the molecule, in which case it is designated as 6aβ, while the 10a-hydrogen atom is oriented below the plane of the molecule, and is designated as 10aα. The mirror image of such orientation is included within the term "6a,10a-trans" and finds the 6a-hydrogen atom below the plane of the molecule, and designated as 6aα, while the 10a-hydrogen atom is oriented above the plane of the molecule, and is referred to as 10aβ. The absolute configuration of the 6a-hydrogen atom and the 10a-hydrogen atom will not hereinafter be designated; rather, it is to be understood that the designation "trans" includes the separate mirror image isomers of the compounds having the above general formula, as well as a mixture of such mirror image isomers. For example, a 6a,10a-trans compound prepared by the process of this invention will be understood to include the 6aα, 10aβ-isomer, as well as the 6aβ,10aα isomer, or a mixture of said mirror images. Such mixture of mirror image isomers will be designated in the normal manner as a dl-mixture.

In accordance with this invention, there is prepared a dl-trans-1-hydroxy-6,6-dimethyl-6,6a,7,8,10,10a-hexahydro-9H-dibenzo[d,b,]pyran-9 one having a alkyl, alkenyl, cycloalkyl, or cycloalkenyl group attached at the C-3 position. Such groups are defined in the above formula by "R", which term includes $C_5$–$C_{10}$ alkyl, $C_5$–$C_{10}$ alkenyl, $C_5$–$C_8$ cycloalkyl, and $C_5$–$C_8$ cycloalkenyl.

The term "$C_5$–$C_{10}$ alkyl" as used herein refers to both straight and branched chain alkyl groups having a total of from five to ten carbon atoms. Examples of such alkyl groups include n-pentyl, 1-methylbutyl, 1,1-dimethylpropyl, n-hexyl, 1,2-dimethylpentyl, 1,1-dimethylhexyl, 1-ethylbutyl, 1-methyl-2-ethylbutyl, 2-methylhexyl, n-heptyl, 1,2-dimethylheptyl, n-octyl, iso-octyl, 1-ethyloctyl, 1,2-dimethyloctyl, n-nonyl, 1,1-dimethylheptyl, and 1,1-dimethyloctyl.

Examples of "$C_5$–$C_{10}$ alkenyl" groups defined by R include both straight and branched chain alkenyl groups such as 1-pentenyl, 1-hexenyl, 2-hexenyl, 1,2-dimethyl-1-heptenyl, 2-(1-octenyl), 2-ethyl-1-hexenyl, 1-ethyl-2-heptenyl, 3-octenyl, 2-methyl-1-nonenyl, 2-nonenyl, 1-decenyl, 2-decenyl, and the like.

The term "$C_5$–$C_8$ cycloalkyl" refers to cycloalkyl groups having from five to eight total carbon atoms, and includes groups such as cyclopentyl, cyclohexyl, cycloheptyl, and cyclooctyl. Similarly, the term "$C_5$–$C_8$ cycloalkenyl", as used herein, refers to cyclic aliphatic groups having from five to eight carbon atoms, and having one site of unsaturation. Typical examples of such groups include 1-cyclopentenyl, 1-cyclohexenyl, 1-cycloheptenyl, 2-cyclooctenyl, and related cycloalkenyl groups.

In accordance with the present invention, a 6a,10a,-cis-1-hydroxy-3-substituted-6,6-dimethyl-6,6a,7,8,10,10a-hexahydro-9H-dibenzo [b,d]pyran-9-one is reacted with an aluminum halide selected from the group consisting of aluminum chloride and aluminum bromide in an unreactive organic solvent to provide the corresponding 6a,10a-trans-1-hydroxy-3-substituted-6,6-dimethyl-6,6a,7,8,10,10a- hexahydro-9H-dibenzo[b,d]-pyran-9-one. While the precise amount of aluminum halide required to effect such conversion is not particularly critical to the process, the epimerization reaction typically is accomplished by commingling the above-named 6a,10a-cis-dibenzo[b,d]pyranone derivative with an excess of the aluminum halide. The excess of aluminum halide routinely utilized in the reaction is an amount in the range of from about a 3 to about a 4 molar excess; however, even a larger excess can be utilized if desired. The reaction generally is carried out in an unreactive organic solvent. Typical examples of which include halogenated hydrocarbons such as chloroform, carbon tetrachloride, dichloromethane, bromomethane, 1,2-dichloroethane, bromoethane, brombenzene, and chlorobenzene; aromatic solvents such as benzene, toluene, nitrobenzene, and xylene; as well as ethers such as diethyl ether and methyl ethyl ether. While the particular solvent utilized in the epimerization reaction of this invention is not of a critical nature, preferred solvents include the halogenated hydrocarbons such as dichloroethane, dichloromethane, bromoethane, and 1,2-dibromoethane; and aromatic solvents such as benzene and toluene.

The process for isomerization of a 6a,10a-cis-hexahydrodibenzo[b,d]pyranone to the corresponding 6a,10a-trans isomer provided by this invention can be carried out within essentially any convenient reaction temperature range, since the precise reaction temperature is not of a critical nature to the process. The process typically is carried out at a temperature within the range of from about −80° to about 100° C., and preferably is conducted at a temperature within the range of from about 0° C. to about 50° C. The reaction time is also not critical to the process. While the reaction is normally substantially complete after about 10 minutes to 6 hours, longer reaction times are apparently not detrimental to the 6a,10a-trans-product which is formed. Routinely, the reaction is continued until the isomerization of the cis-dibenzo[b,d]pyranone to the corresponding trans-dibenzo[b,d]pyranone is substantially complete, for example as demonstrated by monitoring the progress of the reaction by normal methods such as thin layer chromatographic analysis. After the conversion of the cis-isomer to the desired trans-isomer is complete, the product is readily isolated by removal of any excess aluminum halide, for instance by washing the reaction mixture with water or with an aqueous acid solution such as dilute aqueous hydrochloric or sulfuric acid. The solvent can then be removed from the reaction mixture, for instance by evaporation, thus providing the desired 6a,10a-trans-1-hydroxy-3-substituted-6,6-dimethyl-6,6a,7,8,10,10a-hexahydro-9H-dibenzo[b,d]pyran-9-one, generally as one dl-mixture. The product thus formed is substantially free of foreign contaminants but can be further purified if desired by conventional techniques such as solid-liquid chromatography, thick-layer chromatography, and recrystallization from common solvents such as hexane and cyclohexane.

As hereinbefore indicated, the process of this invention can be, and typically is, carried out on a dl-mixture mixture of 6a,10a-cis-hexahydrodibenzo[b,d]pyranones to provide the corresponding dl-mixture of 6a,10a-trans-hexahydrodibenzo[b,d]pyranones. Accordingly, some typical examples of dl-trans-1-hydroxy-3-substituted-6,6-dimethyl-6,6a,7,8,10,10a-hexahydro-9H-dibenzo[b,d]pyran-9-ones which are readily prepared by the process of this invention include the following:

dl-trans-1-hydroxy-3-n-heptyl-6,6-dimethyl-6,6a,7,8,10,10a-hexahydro-9H-dibenzo[b,d]-pyran-9-one;

dl-trans-1-hydroxy-3-(1,2-dimethylheptyl)-6,6-dimethyl-6,6a,7,8,10,10a-hexahydro-9H-dibenzo[b,d]-pyran9-one;

dl-trans-1-hydroxy-3-(1-ethylhexyl)-6,6-dimethyl-6,6a,7,8,10,10a-hexahydro-9H-dibenzo[b,d]pyran-9-one;

dl-trans-1-hydroxy-3-(1-methyl-1-heptneyl)-6,6-dimethyl-6,6a,7,8,10,10a-hexahydro-9H-dibenzo[b,d]-pyran-9-one;

dl-trans-1-hydroxy-3-(1,2-dimethyl-1-hexenyl)-6,6-dimethyl-6,6a,7,8,10,10a -dibenzo[b,d]pyran-9-one;

dl-trans-1-hydroxy-3-(1,1-dimethyl-2-propenyl)- 6,6-dimethyl 6,6a7,8,10,10a -hexahydro-9-H-dibenzo[b,d]-pyran-9-one;

dl-trans-1-hydroxy-3-cyclopentyl-6,6-dimethyl-6,6a,7,8,10,10a-hexadhydro-9H-dibenzo[b,d]-pyran-9-one;

dl-trans-1-hydroxy-3-cyclohexyl-6,6-dimethyl-6,6a,7,8,10,10a-hexahydro-9H-dibenzo[b,d]pyran-9-one;

dl-trans-1-hydroxy-3-cyclooctyl-6,6-dimethyl-6,6a,7,8,10,10a-hexahdyro-9H-dibenzo[b,d]pyran-9-one;

dl-trans-1-hydroxy-3-(1-cyclohexenyl)-6,6-dimethyl-6,6a,7,8,10,10a-hexahydro-9H-dibenzo[b,d]pyran-9-one;

dl-trans-1-hydroxy-3-1-cycloheptenyl)-6,6-dimethyl-6,6a,7,8,10,10a-hexahydro-9H-dibenzo[b,d]pyran-9-one; and dl-trans-1-hydroxy-3-(2-cycloheptenyl)-6,6-dimethyl-6,6a,7,8,10,10a-hexahdyro-9H-dibenzo[b,d]pyran-9-one.

The cis-1-hydroxy-3-substituted-6,6-dimethyl-6,6a,7,8,10,10a-hexahydro-9H-dibenzo[b,d]pyran-9-ones which are the required starting materials for the process of this invention can be prepared by any of a number of methods. The 3-n-pentyl derivative, for instance, was prepared in low yields by Fahrenholtz as described in U.S. Pat. Nos. 3,507,885 and 3,636,058. Other 3-substituted derivatives can be prepared according to the procedure taught by Fahrenholtz by selecting the appropriately 5-substituted resorcinol.

Alternatively, the required 6a,10a-cis-hexahydrodibenzo[b,d]pyran-9-ones can be prepared by the condensation of a 5-substituted resocinol with 1-methoxy-4-(1-hydroxy-1-methylethyl)-1,4-cyclohexadiene in the presence of excess boron trifluoride etherate or stannic chloride. The condensation generally is accomplished by mixing approximately equimolar quantities of the 5-substituted resorcinol and the 1-methoxy-4-(1-hydroxy-1-methylethyl)-1,4,-cyclohexadiene in a solvent such as benzene, and adding to the reaction mixture about a 1 to about a 5 molar excess of boron trifluoride diethyl etherate or stannic chloride. The reaction typically is carried out at about 25° C., and generally is substantially complete after about 4 or 5 hours. The product, a dl-cis-1-hydroxy-3-substituted-6,6-dimethyl-6,6a,7,8,10,10a-hexahydro-9H-dibenzo[b,d]pyran-9-one, is readily isolated by removing the reaction solvent, followed by crystallization.

Example of 5-substituted resorcinols commonly used in the preparation of the required cis-1-hydroxy-3-substituted-6,6-dimethyl-6,6a,7,8,10,10a-hexahydro-9H-dibenzo[b,d]pyran-9-one according to the above-described condensation reaction or according to the method taught by Fahrenholtz include 5-n-pentyl resorcinol, 5-n-octyl resorcinol, 5-(1,2-dimethylheptyl)resorcinol, 5-(1-propylbutyl)-resorcinol, 5-(2-methyl-2-hexenyl)resorcinol, 5-(1,2-dimethyl-1-heptenyl)resorcinol, 5-(2-hexenyl)resorcinol, 5-(1-ethyl-1-heptenyl)resorcinol, 5-(2-decenyl)resorcinol, 5-cyclopentyl resorcinol, 5-cycloheptyl resorcinol, 5-cyclooctyl resorcinol, 5-(1-cyclooctenyl)resorcinol, 5-(1-cycloheptenyl)resorcinol, and 5-(2-cyclopentenyl)resorcinol.

The 1-methoxy-4-(1-hydroxy-1-methylethyl)-1,4-cyclohexadiene which is condensed with the above-named 5-substituted resorcinol is easily prepared by carrying out a standard Birch reduction on 1-methoxy-4-(1-hydroxy-1-methylethyl)benzene, as described for instance by Inhoffen et al., Ann. 674, 28–35 (1964).

As hereinbefore pointed out, the dl-trans-1-hydroxy-3-substituted-6,6-dimethyl-6,6a,7,8,10,10a-hexahydro-9H-dibenzo[b,d]pyran-9-ones which are prepared by the process of this invention are useful as pharmaceutical agents and also as intermediates in the preparation of other valuable drugs. A number of the 6a,10a-trans-dibenzo[b,d]-pyran-9-ones prepared by the process of this invention are especially useful as anti-anxiety drugs, and additionally are useful in the treatment of depression, as well as having the ability to provide sedation and analgesia to subjects in need of such treatment. Of particular importance among this group of compounds is dl-trans-1-hydroxy-3-(1,1-dimethyl-heptyl)-6,6-dimethyl-6,6a,7,8,10,10a-hexahydro-9H-dibenzo[b,d]-pyran-9-one, which compound is especially useful as an anti-anxiety agent and can be utilized as a tranquilizer for subjects suffering from neurotic anxiety. The usefulness of this latter compound, in addition to related compound, has been demonstrated in standard laboratory tests which are used to detect anti-anxiety activity. Specifically, the above-named compound has demonstrated a minimum effective dose of 1.25 mg. per kg. of body weight when administered orally for taming septal-lesioned rats.

The process of this invention accordingly provides compounds which can be administered to subjects suffering from anxiety and in need of treatment. The compounds preferably are formulated ffor oral administration, however, parenteral administration can also be used. Normal daily dosages are from 0.1 to about 100 mg. per subject. The compounds are formulated in a conventional manner using common excipients and carriers such as starch, dextrose, polyvinylpyrrolidone, and the like. The formulations can be molded into tablets, or encapsulated into empty gelatin capsules for convenient oral administration, or made into solutions or suspensions for parenteral administration. As an example of a preferred mode of oral administration, 10 parts of a compound prepared by the process of this invention, such as dl-trans-1-hydroxy-3-(1,1-dimethylheptyl)-6,6a,7,8,10,10a-hexahydro-6,6-dimethyl-9H-dibenzo[b,d]-pyran-9-one, is admixed with 90 parts of polyvinylpyrrolidone in ethanol. The ethanol then is removed by evaporation, thus providing a solid which then is mixed with 89 parts of starch and 1 part of polyoxyethylenesorbitan monooleate. The mixture so prepared is encapsulated so that each capsule contains about 5 mg. of the active drug. A subject then is administered one or two capsules per day, or as needed, so as to impart to the subject a tranquilizer effect.

Additionally, as pointed out hereinabove, the 6a,10a-trans-dibenzo[b,d]pyran-9-ones prepared by the process of this invention are useful as intermediates in the synthesis of other valuable dibenzo[b,d]pyran derivatives. More particularly, reduction of the 9-keto group provides certain compounds which are useful as blood-pressure lowering agents. For example, reduction of dl-trans-1-hydroxy-3-(1,1-dimethylheptyl)-6,6-dimethyl-6,6a,7,8,10,10a-hexahydro-9H-dibenzo[b,d]pyran-9-one provides dl-trans-3-(1,1-dimethylheptyl)-6,6-dimethyl-6a,7,8,10,10a-hexahydro- 6H-dibenzo[b,d]pyran-1,9-diol, which compound is of particular pharmacological importance due to its hypotensive activity.

The compounds provided by the process of this invention additionally are useful in the synthesis of drugs possessing central nervous system activity. Reaction of 6a,10a-trans-dibenzo[b,d]pyran-9-ones with methyl magnesium bromide, followed by dehydration, provides a group of trans-1-hydroxy-3-substituted-6,6,9-trimethyl-6a,7,8,10,10a-tetrahydro-6H-dibenzo[b,d]pyran, many of which are useful CNS agents, as set forth for example in U.S. Pat. No. 3,507,885.

The following detailed examples are included to better illustrate various aspects of the novel process provided by this invention, including the preparation of the cis starting materials. The examples are purely illustrative, and should not be construed as limiting the present invention in any way.

EXAMPLE 1 dl-cis-1-Hydroxy-3-(1,1-dimethylheptyl)-6,6-dimethyl-6,6a,7,8,10,10a-hexahydro-9H-dibenzo[b,d]pyran-9-one.

A solution of 504 mg. of 1-methoxy-4-(1-hydroxy-1-methylethyl)-1,4-cyclohexadiene and 708 mg. of 5-(1,1-dimethylheptyl)resorcinol in 25 ml. of benzene was stirred at 24° C. while 5 ml. of boron trifluoride diethyl etherate was added in one portion. The reaction mixture was stirred at 24° C. for five hours. The reaction mixture then was added to 20 ml. of 6N hydrochloric acid solution. After allowing the benzene solvent to evaporated from the aqueous acid solution, the solution was extracted several times with diethyl ether. The ethereal extracts were combined, washed with water and with aqueous sodium bicarbonate solution, and dried. Evaporation of the solvent under reduced pressure provided an oil, which was crystallized from hexane to afford dl-cis-1-hydroxy-3-(1,1-dimethylheptyl)-6,6-dimethyl-6,6a,7,8,10,10a-hexahydro-9H-dibenzo[b,d]pyran-9-one.

nmr (CDCl$_3$): 80 Hz (s, 3H, C-6 -methyl), 84 Hz (s, 3H, C-6 -methyl).

EXAMPLE 2 dl-cis-1-Hydroxy-3-n-pentyl-6,6-dimethyl-6,6a,7,8,10,10a-hexahydro-9H-dibenzo[b,d]pyran-9-one.

A solution of 2.66 g. of 1-methoxy-4-(1-hydroxy-1-methylethyl)-1,4-cyclohexadiene and 2.9 g. of 5-n-pentyl resorcinol (olivetol) in 110 ml. of dichloromethane containing a trace amount of cyclohexane was cooled to −5° C. in an ice/brine bath and stirred. While stirring the reaction mixture at −5° C., 4.2 ml. of stannic chloride was added to the mixture in one portion. The reaction mixture was then allowed to warm to room temperature, and stirring of the mixture was continued for seven hours. The reaction mixture then was washed with water and with 1N sodium hydroxide solution, and dired. Removal of the solvent by evaporation under reduced pressure provided the product as an oil. The oil was crystallized from 10 ml. of n-hexane to provide dl-cis-1-hydroxy-3-n-pentyl-6,6-dimethyl-6,6a,7,8,10,10a-hexahydro-9H-dibenzo[b,d]pyran-9-one.

nmr (CDCl$_3$) 80 Hz (s, 3H, C-6 methyl), 84 Hz (s, 3H, C-6 methyl).

EXAMPLE 3 dl-trans-1-Hydroxy-3-(1,1-dimethylheptyl)-6,6-dimethyl-6,6a,7,8,10,10a-hexahdyro-9H-dibenzo[b,d]pyran-9-one.

A solution of 1.0 g. of dl-cis-1-hydroxy-3-(1,1-dimethylheptyl)-6,6-dimethyl-6,6a,7,8,10,10a-hexahydro-9H-dibenzo[b,d]pyran-9-one in 40 ml. of commercial grade dichloromethane was stirred at 24° C. while 1.0 g. of aluminum chloride was added in one portion. The reaction mixture was stirred at 24° C. for five hours. The reaction mixture was then washed with 1N hydrochloric acid solution and with water. After drying the organic solution, the solvent was removed therefrom by evaporation under reduced pressure, providing 994 mg. of the product as a solid. The solid so formed was recrystallized from hexane to afford 761 mg. of dl-trans-1-hydroxy-3-(1,1-dimethylheptyl)-6,6-dimethyl-6,6a,7,8,10,10a-hexahydro-9H-dibenzo[b,d]pyran-9-one. M.P. 160°–161° C.

EXAMPLE 4 dl-trans-1-hydroxy-3-n-pentyl-6,6-dimethyl-6,6a,7,8,10,10a-hexahydro-9H-dibenzo[b,d]pyran-9-one.

A solution of 400 mg. of dl-cis-1-hydroxy-3-n-pentyl-6,6-dimethyl-6,6a,7,8,10,10a-hexahdyro-9H-dibenzo[b,d]pyran-9-one in 200 ml. of dichloromethane containing 1 ml. of cyclohexane was stirred at 24° C. while 600 mg. of aluminum chloride was added in one portion. The reaction mixture then was stirred at 24° C. for two hours. After washing the reaction mixture with water and then drying the organic solution, the solvent was removed by evaporation under reduced pressure, leaving the product as a solid. The solid so formed was crystallized from n-hexane to afford 220 mg. of dl-trans-1-hydroxy-3-n-pentyl-6,6-dimethyl-6,6a,7,8,10,10a-hexahydro-9H-dibenzo[b,d]pyran-9-one. M.P. 146°–150° C.

nmr (CDCl$_3$) 67 Hz (s, 3H, C-6 methyl), 88 Hz (s, 3H, C-6 methyl).

EXAMPLE 5 dl-trans-1-hydroxy-3-(1,1-dimethylheptyl)-6,6-dimethyl-6,6a,7,8,10,10a-hexahydro-9H-dibenzo[b,d]pyran-9-one.

To a solution of 1.0 g. of dl-cis-1-hydroxy-3-(1,1-dimethylheptyl)-6,6-dimethyl-6,6a,7,8,10,10a-hexahydro-9H-dibenzo[b,d]pyran-9-one in 40 ml. of dichloromethane was added in one portion 1.0 g. of aluminum bromide. The reaction mixture was stirred for five hours at 24° C., and then was washed with 1N hydrochloric acid solution and with water. The reaction mixture was dried and the solvent was removed by evaporation under reduced pressure, thus providing dl-trans-1-hydroxy-3-(1,1-dimethylheptyl)-6,6-dimethyl-6,6a,7,8,10,10a-hexahydro-9H-dibenzo[b,d]pyran-9-one.

nmr (CDCl$_3$) 67 Hz (s, 3H, C-6 methyl), 88 Hz (s, 3H, C-6 methyl).

EXAMPLE 6 dl-trans-1-Hydroxy-3-(2-cyclohexenyl)-6,6-dimethyl-6,6a,7,8,10,10a-hexahydro-9H-dibenzo[b,d]pyran-9-one dl-cis-1-hydroxy-3-cyclohexyl-6,6-dimethyl-6,6a,7,8,10,10a-hexahydro-9H-dibenzo[b,d]pyran-9-one was treated with aluminum bromide in chlorobenzene according to the process of Example 5 to provide dl-trans-1-hydroxy-3-cyclohexyl-6,6-dimethyl-6,6a,7,8,10,10a-hexahydro-9H-dibenzo[b,d]pyran-9-one.

EXAMPLE 7 dl-trans-1Hydroxy-3(2-cyclohexenyl)-6,6-dimethyl-6,6a,7,8,10,10a-hexahydro-9H-dibenzo[b,d]pyran-9-one By following the process of Example 5, dl-cis-1-hydroxy-3-(2-cyclohexenyl)-6,6-dimethyl-6,6-dimethyl-6,6a,7,8,10,10a-hexahydro-9H-dibenzo[b,d]pyran-9-one was reacted with aluminum bromide in nitromethane to afford dl-trans-1-hydroxy-3-(2-cyclohexenyl)-6,6-dimethyl-6,6a,7,8,10,10a-hexahydro-9H-dibenzo[b,d]-pyran-9-one.

We claim:

1. A process for preparing a 6a,10,a-trans-hexahydrodibenzo[b,d]pyran-9-one of the general formula

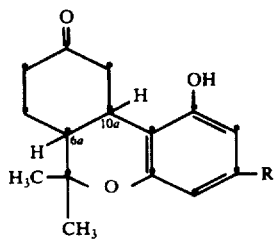

wherein:

R is $C_5$–$C_{10}$ alkyl, $C_5$–$C_{10}$ alkenyl, $C_5$–$C_8$ cycloalkyl, or $C_5$–$C_8$ cycloalkenyl; and wherein the hydrogen atoms attached at the 6a and 10a positions are oriented trans to one another; comprising reacting the corresponding 6a,10a-cis-hexahydrodibenzo[b,d]-pyran-9-one with an aluminum halide selected from the group consisting of aluminum chloride and aluminum bromide, in an unreactive organic solvent, at a temperature ranging from about −80° to about 100° C., for a period of time ranging from about 10 minutes to about 6 hours.

2. The process according to claim 1 wherein the aluminum halide is aluminum chloride.

3. The process according to claim 2 wherein the solvent is a halogenated hydrocarbon.

4. The process according to claim 3 wherein the reaction is carried out at a temperature ranging from about 0° C. to about 50° C.

5. The process according to claim 1, said process comprising reacting dl-cis-1-hydroxy-3-(1,1-dimethylheptyl)-6,6-dimethyl-6,6a,7,8,10,10a-hexahydro-9H-dibenzo[b,d]-pyran-9-one with aluminum chloride in dichloromethane to form dl-trans-1-hydroxy-3-(1,1-dimethylheptyl)-6,6-dimethyl-6,6a,7,8,10,10a-hexahydro-9H-dibenzo[b,d]-pyran-9-one.

* * * * *